United States Patent

Inouye et al.

[11] 4,018,753
[45] Apr. 19, 1977

[54] POLYPEPTIDES WITH ACTH-LIKE ACTIVITIES

[75] Inventors: Ken Inouye; Masaru Shin, both of Kobe; Kunio Watanabe, Otsu, all of Japan

[73] Assignee: Shionogi & Co., Ltd., Osaka, Japan

[22] Filed: July 16, 1975

[21] Appl. No.: 596,245

[30] Foreign Application Priority Data

July 30, 1974 Japan .................. 49-87759

[52] U.S. Cl. .................. 260/112.5 R; 424/179
[51] Int. Cl.$^2$ ............... C07C 103/52; A61K 37/40
[58] Field of Search .................. 260/112.5 R

[56] References Cited

UNITED STATES PATENTS

| | | | |
|---|---|---|---|
| 3,651,039 | 3/1972 | Fujino et al. | 260/112.5 R |
| 3,761,459 | 9/1973 | Pless et al. | 260/112.5 R |
| 3,761,461 | 9/1973 | Pless et al. | 260/112.5 R |
| 3,770,715 | 11/1973 | Tesser et al. | 260/112.5 R |
| 3,792,033 | 2/1974 | Iselin et al. | 260/112.5 R |
| 3,873,511 | 3/1975 | Otsuka et al. | 260/112.5 R |

Primary Examiner—Lewis Gotts
Assistant Examiner—Reginald J. Suyat
Attorney, Agent, or Firm—Wenderoth, Lind & Ponack

[57] ABSTRACT

A polypeptide of the formula:

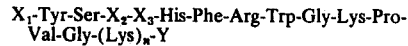

wherein $X_1$ is α-aminoisobutyric acid, β-alanine, L-serine, glycine, D-serine, D-alanine, γ-aminobutyric acid or sarcosine residue; $X_2$ is L-methionine, L-norleucine, L-isoleucine or L-norvaline residue; $X_3$ is L-glutamic acid or L-glutamine residue; n is an integer of 1-4 and Y is a group of

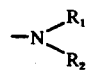

which is linked to the carbonyl group of the C-terminal lysine residue, wherein $R_1$ and $R_2$ are each hydrogen or the same or different lower alkyl having 1-5 carbon atoms, and $R_1$ and $R_2$, when taken together with or without another hetero atom, form a substituted or unsubstituted nitrogen containing heterocyclic ring, with the proviso that a peptide when $X_1$ is a α-aminoisobutyric acid or D-serine, $R_1$ and $R_2$ are each hydrogen and n is 4 is excluded; non-toxic acid addition salts thereof and complexes thereof; being useful as a medicament owing to their strong adrenal-stimulating activity with protracted action and little side effects. They can be prepared by condensing the amino acids together one by one or by condensing the small peptide fragments together in a per se conventional manner.

4 Claims, No Drawings

POLYPEPTIDES WITH ACTH-LIKE ACTIVITIES

This invention relates to new polypeptides having strong ACTH-like properties, particularly adrenal-stimulating activity, with protracted activity and little side effects; non-toxic acid addition salts thereof; and complexes thereof; and to a process for the production of the same. The polypeptides of the invention can be represented by the formula:

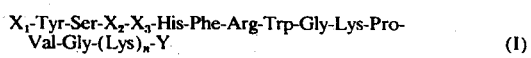

wherein $X_1$ is a α-aminoisobutyric acid, β-alanine, L-serine, glycine, D-serine, D-alanine, γ-aminobutyric acid or sarcosine residue; $X_2$ is L-methionine, L-norleucine, L-isoleucine or L-norvaline residue; $X_3$ is L-glutamic acid or L-glutamine residue; $n$ is an integer of 1–4; and Y is a group represented by the formula

which is linked to the carbonyl group of the C-terminal lysine residue, wherein $R_1$ and $R_2$ are each hydrogen or the same of different lower alkyl group having 1–5 carbon atoms (e.g. methyl, ethyl, propyl), and $R_1$ and $R_2$, when taken together with or without another hetero atom, form a substituted or unsubstituted nitrogen containing hererocyclic ring (e.g. pyrrolidine, proline, prolinol, proline amide), with the proviso that a peptide when $X_1$ is α-aminoisobutyric acid or D-serine, $R_1$ and $R_2$ are each hydrogen and $n$ is 4 is excluded. Among the polypeptides (I), preferred polypeptides are [Aib$^1$, Lys$^{17,18}$]-ACTH(1–18)-N(CH$_3$)$_2$,

and [Aib$^1$,Lys$^{17,18}$]-ACTH(1–19)-NH$_2$(Aib=α-aminoisobutyric acid).

Up to the present, a number of modified ACTH polypeptides which possess chain length shorter than that of native hormone (ACTH) and exhibit ACTH-like action have been reported. In such peptides, modifications are directed mainly to the positions 1, 4, 5, 15, 16, 17, 18 and to their C-terminal residue. For example, the first amino acid L-serine can be substituted by α-aminoisobutyric acid, D-serine, β-alanine, glycine or sarcosine; the fourth amino acid L-methionine by L-norleucine L-isoleucine, or L-norvaline; the fifth amino acid L-glutamic acid by L-glutamine; the fifteenth and the sixteenth amino acids L-lysines by L-ornithines; the seventeenth and the eighteenth amino acids L-arginines by L-lysines or L-ornithines; and the carboxyl group of the C-terminal amino acid is in the form of amide. However, one of the drawbacks of these peptides is that they exhibit rather strong melanocyte-stimulating activity compared to their adrenal-stimulating activity. Since all the corticotropically active polypeptides contain in the molecule the amino acid sequence responsible for the melanocyte-stimulating activity, they exhibit more or less such undesirable activity. Thus, when patients receive such peptide having strong melanocyte-stimulating activity, the skin of patients is darkened.

In addition, when corticotropically active peptides are used as a drug for therapeutical purposes, they are usually administered in the form of a complex with zinc. The reason that the said complexes have been employed in the field consists in the fact that they show protracted action, compared to the corresponding plain peptide. However, several reports have been recently published to indicate that a dangerous anaphylactic reaction may occur with such a complex of ACTH peptide with zinc more often than with the plain peptide. In this respect, a plain peptide having a long-lasting adrenal-stimulating action at a high activity level is quite desirable from its therapeutical view point. The peptide is also desirable to be a weak melanocyte-stimulating agent.

In the course of the investigations to solve the above problems of corticotropically active polypeptides, the present inventors have discovered that, in addition to the replacements of the amino acid residues at positions 1, 17, and 18 of the peptide, further modification at the C-terminal improves its biological properties to lead to the enhancement of potency and the prolongation of action with little side effects.

According to the invention, the desired polypeptides (I) can be prepared by condensing the amino acids together one by one or by condensing the small peptide fragments together in a per se conventional manner. More particularly, they can be prepared by (a) condensing an amino acid ester or peptide ester having a free amino group with other amino acid or peptide having protected amino group(s) in the presence of a condensing agent, or (b) reacting an amino acid or peptide having a free amino group and protected or unprotected carboxyl group(s) with other amino acid or peptide having an activated carboxyl group and protected amino groups, and removing the protecting groups from the resulting protected peptide by catalytic hydrogenolysis, acid solvolysis, hydrolysis, hydrazinolysis, sodium in liquid ammonia reduction or other means.

Peptide-bonds are formed by the usual methods. Examples of said methods are the azide method, the dicyclohexylcarbodiimide method, the carbonyldiimidazole method, the mixed anhydride method, the activated ester method (e.g. p-nitrophenyl ester method, N-hydroxysuccinimide ester method, cyanomethyl ester method, p-nitrophenyl thiol ester method, pentachlorophenyl ester method), the isoxazolium method, the N-carboxyanhydride method and the like. The desired peptides are also prepared by the so-called solid phase peptide synthesis. Although above-mentioned methods can be employed for the formation of any peptide bond in preparing the present polypeptides, the most commonly practised methods are the dicyclohexylcarbodiimide method, the azide method, the mixed anhydride method and the activated ester method. In the coupling reaction mentioned above, N-hydroxysuccinimide, N-hydroxy-5-norbornene-2,3-dicarboxyimide or 1-hydroxybenzotriazole may be added.

In the production of the desired polypeptides, any free functional groups not participating in the reaction are advantageously protected, especially by such groups that can be easily removed by hydrogenolysis, acidolysis, hydrazinolysis, hydrolysis, or sodium in liquid ammonia reduction. The carboxyl group is advantageously protected by esterification, for example, with a lower alkanol (e.g. methanol, ethanol, propanol, t-butanol) or an aralkanol (e.g. benzyl alcohol, p-nitrobenzyl alcohol, p-methoxybenzyl alcohol). These carboxyl-protecting groups are introduced by the usual method.

The amino group is protected preferably by introducing a group such as 1-methylcyclohexyloxycarbonyl group, 1-methyl-cyclopentyloxycarbonyl group, 9-methyl-9-fluorenyloxycarbonyl group, t-butyloxycarbonyl group, t-amyloxycarbonyl group, o-nitrophenylsulphenyl group, 2-(p-diphenyl)isopropyloxycarbonyl group, benzyloxycarbonyl group, tosyl group, formyl group or trityl group, in a conventional manner. For the protection of the guanidyl group of arginine, nitro group, tosyl group or adamantyloxycarbonyl group is preferably employed, but the protection of the guanidyl group is not always necessary. The $\epsilon$-amino group of lysine is advantageously protected by such amino-protecting groups as those mentioned above. However, it is desirable to choose an $\omega$-amino protecting group which is selectively removable from that of $\alpha$-amino protecting group. The $\gamma$-carboxyl group of glutamic acid is preferably protected by such carboxyl-protecting groups as mentioned above and the imidazole group of histidine may be protected by tosyl group, benzyloxycarbonyl group, benzyl group or the like. Further, the hydroxy group of serine or tyrosine may be protected by acetyl group, benzyl group or t-butyl group, but such protection is not always necessary.

Removal of the protecting groups from the amino acids, intermediate fragments or from the polypeptides in the last stage is carried out in a per se conventional manner employed in the field of peptide chemistry. Examples of such methods are catalytic hydrogenolysis, sodium in liquid ammonia reduction, acid solvolysis using an acid (e.g. hydrogen fluoride, hydrogen bromide, hydrogen chloride, trifluoroacetic acid, acetic acid, formic acid), acid hydrolysis (with hydrochloric acid, hydrobromic acid) and saponification with an alkali (e.g. sodium hydroxide).

The final coupling reaction for producing the desired polypeptides (I) is performed, for example, by condensing a protected decapeptide of the formula:

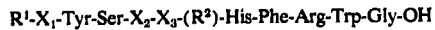

wherein $R^1$ is an amino-protecting group and $R^2$ is a protecting group for the $\gamma$-carboxyl group of the glutamic acid, and $X_1$, $X_2$ and $X_3$ have each the same meaning as defined above, with a protected peptide of the formula:

wherein $R^3$ and $R^4$ are each an $\epsilon$-amino-protecting group, and Y and $n$ have each the same meaning as defined above, by the activated ester method, the azide method, the dicyclohexylcarbodiimide method, the mixed anhydride method or a combination method thereof; and removing all the protecting groups from the resultant protected peptide of the formula:

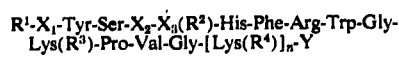

wherein all the sumbols have each the same meaning as defined above, by acid solvolysis, catalytic hydrogenolysis, or sodium in liquid ammonia reduction.

The final coupling reaction is preferably carried out by the activated ester method, particularly the N-hydroxy-succinimide ester method, in an inert solvent at a temperature of $-20°$ C to $60°$ C, especially $0°$ C to $45°$ C, for about 1 hour to 72 hours, especially for about several hours to 48 hours. Examples of the solvent used are dimethylformamide, dimethylsulfoxide, hexamethylphosphortriamide, and an aqueous solvent thereof, and a mixed solvent thereof. The protecting groups are removed preferably by acid solvolysis using an acid such as hydrogen halide (e.g. hydrogen fluoride, hydrogen bromide, hydrogen chloride) trichloroacetic acid or trifluoroacetic acid at $-20°$ C to $60°$ C for 30 minutes to several hours.

The polypeptides prepared by the present invention can be purified by ion-exchange chromatography, partition chromatography, exclusion chromatography, or by adsorption chromatography on a column of ion-exchange resin, ion-exchange cellulose, cellulose, cross-linked dextran gel (e.g. Sephadex), polyacrylamide gel (e.g. Bio-Gel P), silica gel or other suitable material usually employed in the field of peptide chemistry.

The novel polypeptides of the invention are produced in the form of a free base or its salt, depending on the purification processes used. Naturally, the salts can be converted into the free base, and to the contrary, the free base can be converted into the acid addition salt by treatment with a suitable acid in a conventional manner. Examples of the acid are inorganic acids such as hydrohalic acid (e.g. hydrochloric acid, hydrobromic acid) or phosphoric acid, and organic acids such as formic acid, acetic acid, propionic acid, succinic acid, citric acid, benzene-sulfonic acid, or p-toluenesulfonic acid. An equimolar or excess amount of acid may be used in such salt formation.

The polypeptides of the present invention can be converted into the corresponding complex with a complex-forming heavy metal (e.g. zinc, copper, iron, nickel, cobalt) or a complex-forming polyamino acid (e.g. poly-glutamic acid, polyaspartic acid, copoly-glutamyl-tyrosine, copoly-aspartyl-glutamic acid) in a per se conventional manner. The complex thus obtained shows long-lasting action.

The polypeptides of the present invention show excellent biological properties which are superior to those of native corticotropin and those of the related peptides ever known.

Assays for adrenal-stimulating activity of the present polypeptides were carried out according to the different methods, comparing with that of native corticotropin (ACTH), [Gly$^1$]-ACTH(1–18)-NH$_2$[Bull.Chem.-Soc.Japan 43 196 (1970)], [Aib$^1$]-ACTH(1–18)-NH$_2$[ibid., 43, 3873 (1970)], [Aib$^1$,Lys$^{17,18}$]-ACTH(1–18)-NH$_2$, Cortrosyn$^R$(N.V.Organon, Netherland) and Cortrosyn-Z (N.V.Organon, Netherland). The adrenal-stimulating activity by the intravenous administration to hypophysectomized rat was determined in such a manner that a peptide preparation was injected into the femoral vein and a blood sample was collected from the abdominal aorta 30 minutes after the injection. The adrenal-stimulating activity by the intramuscular administration to hypophysectomized rat was also determined, where a peptide preparation was injected into the thigh muscle and a blood sample was collected from the abdominal aorta 30 minutes after injection. Throughout the experiment, the USP Corticotropin Reference Standard was used as a standard and the production of 11-hydroxycorticosteroids was determined by the fluorophotometric method of Peterson [J.Biol. Chem. 225 25 (1957)]. For each assay method several determinations were usually performed and the data obtained independently were submitted to the statistical treatment by Sheps and Moore procedure [J.Pharmacol. Extl. Therap. 128, 99 (1960)].

The effect on adrenal growth and thymus involution was determined in the following manner: peptides were intramuscularly injected into rats at a dose of 20 $\mu$g and 100 $\mu$g/rat/day respectively for 2 days. The rats were then submitted to autopsy 24 hours after the last injection, and then the adrenal and thymus were weighed respectively.

The in vivo melanocyte-stimulating activity was determined according to the method described in Endocrinol. Japonica 19, 383 (1972).

The test results are shown in the following table.

The polypeptides, the acid addition salts and the complexes can be administered orally or parenterally in per se conventional forms, e.g. injection, liquid, suspension, emulsion, or aerosol, optionally with suitable carriers, stabilizers, emulsifiers, preseratives, buffers, isotonizing agents and/or wetting agents, where a therapeutically active amount of the active ingredient is contained.

Thus, the present invention includes a pharmaceutical or veterinary preparation comprising a compound in accordance with the invention and an inert pharmaceutical excipient.

The effective dose can be easily determined by a physician on the basis of the data herein-described. Thus, a typical clinical dosage range for the polypeptides of the invention is approximately 0.001 mg/kg to 0.02 mg/kg per day for a normal adult. The present polypeptides are advantageously administered in injec-

| Peptide | Adrenal-stimulating activity | | effect on adrenal growth and thymus a) involution | Melanocyte-stimulating activity b) in vivo | a/b |
|---|---|---|---|---|---|
| | i.v. | i.m. | | | |
| [Aib$^1$,Lys$^{17,18}$]— ACTH(1–18)—N⟨ | 6.8 | 16.5 | 0.41 | 0.25 | 1.64 |
| [Aib$^1$,Lys$^{17,18}$]— ACTH(1–18)—N⟨CH$_3$/CH$_3$ | 8.5 | 11.1 | 0.30 | 0.11 | 2.73 |
| Native ACTH | 1.0 | 4.0 | * | | |
| [Gly$^1$]—ACTH(1–18)—NH$_2$ | 1.0 | 1.0 | * | 0.11 | |
| [Aib$^1$]—ACTH(1–18)—NH$_2$ | 4.1 | 9.9 | 0.12 | 1.00 | 0.12 |
| [Aib$^1$,Lys$^{17,18}$]—ACTH(1–18)—NH$_2$ | 9.3 | 9.4 | 0.40 | 0.82 | 0.49 |
| Cortrosyn | 1.8 | 3.1 | * | | |
| Cortrosyn—Z | | | | 1.00 | 1.72 | 0.58 |

Note:
*The effects on adrenal growth and thymus involution are very weak. Cortrosyn*=ACTH(1–24)—OH (N.V. Organon, Netherlands), Cortrosyn—Z = Zinc complex of Cortrosyn (N.V. Organon, Netherlands). The adrenal-stimulating activity and melanocyte-stimulating activity are expressed in terms of the relative potency.

There are several methods for determining the adrenal-stimulating activity which is the main role of ACTH, and the most reliable method for the examination of such activity is, among others, a test method which studies the effect on adrenal growth and thymus involution. Thus, it can be said that the polypeptides having a higher ratio of a/b (a=effect on adrenal growth and thymus involution, b=melanocyte stimulating activity) are desirable. It is to be noted that the effects of native ACTH, [Gly$^1$]-ACTH(1–18)-NH$_2$ and Cortrosyn on adrenal growth and thymus involution are very weak. These peptides may not be suitable as a drug for practical use. As clearly shown in the above table, the polypeptides of the invention is superior to native ACTH and known peptides ever known, in view of its high ratio of a/b.

The polypeptides of the invention are highly useful and advantageous for therapeutical purposes, e.g. in the treatment of varied inflammations, adrenal insufficiency due to pituitary disorder, acute or chronic articular rheumatisms, allergic diseases or adrenarches of human beings and domestic animals, or for testing the adrenocortical function of animals and human beings.

tions as a dosage form, and administration is repeated as often as required in accordance with the physician's indication.

The abbreviated designation of amino acids, peptides and their derivatives used in the present specification and claims accords with the proposals of the IUPAC-IUB Commission of Biochemical Nomenclature [J.Biol. Chem. 241, 2491 (1966), ibid. 242, 555 (1967), ibid, 247, 977 (1972)]. All the amino acid residues are of the L-configuration, unless otherwise indicated.

The analogs of an ACTH peptide comprising the amino acid residues in positions $m$ through $n$ (as numbered from N-terminal) are designated for abbreviation as X-[A$^i$, B$^j$, . . . ]-ACTH($m$-$n$)-Y where [A$^i$, B$^j$, . . . ] denotes substitutions by A, B, . . . for the amino acid residues in positions $i, j, \ldots$ and X and Y are the hydrogen or its substituent of N-terminal $\alpha$-amino group and the hydroxyl or its substituent of C-terminal $\alpha$-carboxyl group, respectively. When X means hydrogen itself the symbols H may be omitted.

The following examples are given solely for the purpose of illustration and are not to be construed as limitation of the invention.

EXAMPLE 1

Aib-Tyr-Ser-Met-Glu-His-Phe-Arg-Trp-Gly-Lys-Pro-Val-Gly-Lys-Lys-Lys-Lys-N(CH$_3$)$_2$
(Aib=α-aminoisobutyric acid) ([Aib$^1$,Lys$^{17,18}$]-ACTH(1–18)-N(CH$_3$)$_2$)

1. Z-Lys(Boc)-Lys(Boc)-N(CH$_3$)$_2$ (I) (Z=benzyloxycarbonyl, Boc=t-butyloxycarbonyl)

N$^\alpha$-Benzyloxycarbonyl-N$^\epsilon$-t-butyloxycarbonyl-L-lysine N-hydroxysuccinimide ester (2.275 g) is dissolved in tetrahydrofuran (15 ml), and the solution is kept at 0° C. After addition of dimethylamine (1.58 g), the resultant mixture is allowed to stand at 0° C for 4 hours. The solution is evaporated in vacuo and the residue is dissolved in a mixture of ethyl acetate and water. The solution is shaken, and the organic layer is separated. The organic solution is dried and evaporated in vacuo to give an oily residue, which is dissolved in methanol (20 ml) and hydrogenolyzed over palladium-black at room temperature for 3 hours. The reaction solution is concentrated in vacuo and the residue is dissolved in dimethylformamide. To the solution is added N$^\alpha$-benzyloxycarbonyl-N$^\epsilon$-t-butyloxycarbonyl-L-lysine N-hydroxy-succinimide ester (1.67 g), and the mixture is allowed to stand at 4° C. overnight. The solution is concentrated in vacuo to give an oily residue, which is chromatographed on a column of silica gel using a mixed solvent of chloroform and methanol (9 : 1 v/v) to give the desired product. Yield 2.07 g, [α]$_D^{25.5}$ −13.8°±0.6° (c 0.979, methanol).

Anal. Calcd. for C$_{32}$H$_{53}$N$_5$O$_8$·H$_2$O: C, 58.78; H, 8.48; N, 10.71. Found: C, 59.14; H, 8.56; N, 10.38.

2. Z-Lys(Boc)-Lys(Boc)-Lys(Boc)-N(CH$_3$)$_2$ (II)

Compound I (1.896 g) is dissolved in methanol (15 ml) and hydrogenolyzed over palladium black catalyst at room temperature for 2.5 hours. After removal of the solvent by evaporation in vacuo, the residue is dissolved in dimethylformamide, and to the solution is added N$^\alpha$-benzyloxycarbonyl-N$^\epsilon$-t-butyloxycarbonyl-L-lysine N-hydroxysuccinimide ester (1.06 g) under cooling with ice. The mixture is allowed to stand at 4° C overnight, then concentrated in vacuo to give an oily residue. The residue is dissolved in ethyl acetate and washed with water, dried, and evaporated in vacuo. The resultant residue is reprecipitated from ethyl acetate-petroleum ether to give the desired product, yield 1.79 g, mp. 68.5°–70.5° C, [α]$_D^{25.5}$ −20.6°±0.6° (c 1.007, methanol).

Anal. Calcd. for C$_{43}$H$_{73}$N$_7$O$_{11}$: C, 59.77; H, 8.52; N, 11.35. Found: C, 59.68; H, 8.50; N, 11.37.

3. Z-Lys(Boc)-Lys(Boc)-Lys(Boc)-Lys(Boc)-N(CH$_3$)$_2$ (III)

Compound II (0.804 g) is dissolved in methanol (5 ml) and hydrogenolyzed in the presence of palladium black at room temperature for 3 hours. The solution is concentrated in vacuo to give an oily residue. The residue is dissolved in dimethyl-formaide (10 ml), and to this solution is added N$^\alpha$-benzyloxy-carbonyl-N$^\epsilon$-t-butyloxycarbonyl-L-lysine N-hydroxysuccinimide ester (0.478 g). The mixture is allowed to stand at 4° C overnight. After removal of the solvent by evaporation in vacuo, the residue is dissolved in ethyl acetate. The solution is washed with water, dried and evaporated in vacuo to give an oily residue, which is reprecipitated from ethyl acetate-petroleum ether to give the desired product, yield 0.935 g, mp. 90°–92° C, [α]$_D^{24.5}$ −23.4°±0.6° (c 1.014, methanol).

Anal. Calcd. for C$_{54}$H$_{93}$N$_9$O$_{14}$: C, 59.37; H, 8.58; N, 11.54. Found: C, 59.44; H, 8.62; N, 11.65.

4. Z-Lys(Boc)-Pro-Val-Gly-Lys(Boc)-Lys(Boc)-Lys(Boc)-Lys(Boc)-N(CH$_3$)$_2$ (IV)

Compound III (0.546 g) is dissolved in methanol and hydrogenolyzed over palladium-black catalyst at room temperature for 3 hours. After removal of the solvent by evaporation in vacuo, there is obtained N$^\alpha$-free tetrapeptide as an oily residue. On the other hand, Z-Lys(Boc)-Pro-Val-Gly-OH (0.317 g) is dissolved in dimethylformamide (5 ml), and to this solution is added N-hydroxysuccinimide (0.058 g). The mixture is stirred under cooling with ice and to this is added a solution of N,N'-dicycylohexylcarbodiimide (0.103 g) in dimethylformamide. The mixture is stirred at 0° C for 30 minutes, and to this solution is added a dimethylformamide solution of the tetrapeptide obtained above. The mixture is stirred at 0° C for 6 hours and allowed to stand overnight. After removal of the solvent by evaporation, the residue is dissolved in ethyl acetate and the solution is washed, dried and concentrated in vacuo to give a residue. The residue is reprecipitated from a mixture of ethyl acetate and petroleum ether and collected by filtration. The precipitates are submitted to chromatography on a column of silica gel using chloroform (200 ml), chloroform-methanol (95:5, 200 ml), chloroform-methanol (9:1, 200 ml) and chloroform-methanol (85:15, 200 ml) as a developing solvent, thereby producing the desired product, yield 0.447 g, mp. 130°–141° C, [α]$_D^{24.5}$ −44.8°±2.5° (c 0.348, methanol).

Anal. Calcd. for C$_{77}$H$_{132}$N$_{14}$O$_{20}$: C, 58.76; H, 8.45; N, 12.46. Found: C, 58.94; H, 8.61; N, 12.19.

5. Aib-Tyr-Ser-Met-Glu-His-Phe-Arg-Trp-Gly-Lys-Pro-Val-Gly-Lys-Lys-Lys-Lys-N(CH$_3$)$_2$[Aib$^1$,Lys$^{17,18}$-ACTH(1–18)-N(CH$_3$)$_2$] (V)

Compound IV (70.8 mg) is dissolved in methanol (5 ml) and hydrogenolyzed in the presence of palladium-black at room temperature for 3 hours. After removal of the solvent of evaporation in vacuo, the resultant N$^\alpha$-free octapeptide is obtained as an oily residue. On the other hand, Boc-Aib-Tyr-Ser-Met-Glu(OBu$^t$)-His-Phe-Arg-Trp-Gly-OH (63.5 mg) (prepared according to the method as described in the specification of Japanese patent application No. 46147/1974 Japanese unexamined patent publication No. 140444/1975 and Japanese patent publication No. 2545/1973) is dissolved in dimethylformamide (1.5 ml), and the solution is cooled with ice. To this solution is added N-hydrochloric acid (0.1 ml), and the mixture is added to ethyl acetate under cooling. The resultant precipitates are collected and dried. Then, the precipitates are redissolved in dimethylformamide (1 ml), and to this solution are added N-hydroxysuccinimide (10.1 mg) and triethylamine (0.006 ml), then cooled with ice. To this solution are added the octapeptide obtained above and N,N'-dicyclohexyl-carbodiimide (31.8 mg) in dimethylformamide (1 ml), and the mixture is kept at 0° C for 2 hours and at room temperature for 22 hours. The solution is added to ethyl acetate (50 ml), and the resultant precipitates are collected by filtration. The precipitates are dissolved in ethyl acetate and lyophilized to give a white powder (115 mg). The powder is dissolved in trichloroacetic acid (2 ml) together with mercaptoethanol (0.1 ml) and anisole (0.1 ml) and the solution is allowed to stand at room temperature for 1 hour. The precipitates formed upon addition of ether are collected and dried to afford the deprotected octadecapeptide. The octadecapeptide is dissolved in water (5 ml) and passed through a column (0.9 × 10 cm) of Amberlite CG-400 with water. The eluates are lyophilized to give a powder (93 mg). The powder is dissolved in water (1.5 ml) and chromatographed on a column (1.5 × 17 cm) of carboxymethyl cellulose using an ammonium acetate buffer (pH 5.82, 1000 ml) having a linear gradient concentration of 0–0.6M. The fractions containing the desired product are combined and lyophilized to give a purified powder (94 mg). The powder is further purified by partition chromatography on a column (2.3 × 41 cm) of Sephadex G-25 (Medium) using a mixed solvent of butanol-acetic acid-pyridine-water (12:3:4:6 by volume) as a developing solvent. The tubes Nos. 18–43 (6 g/tube) are collected, concentrated in vacuo and lyophilized to give the peptide (61 mg).

The peptide obtained above is further purified on a column (1.5 × 30 cm) of carboxymethyl cellulose (Whatman CM-52) with an ammonium acetate buffer (pH6.13, 1000 ml) having a linear gradient concentration of 0.11–0.6M. The eluates (tube Nos. 153–175)(5 g/tube) are collected, concentrated in vacuo and lyophilized to give the desired peptide. Yield 38 mg, $[\alpha]_D^{24.5}$ −62.2°±2.1° (c 0.5, 0.1N acetic acid). Amino acid molar ratio: Lys 4.96 (5), His 1.00 (1), Arg 1.02 (1), Ser 0.92 (1), Glu 0.98 (1), Pro 1.02 (1), Gly 1.93 (2), Val 1.00 (1), Met 0.95 (1), Try 1.03 (1), Phe 0.99 (1), (The figures in parentheses are theoretical value). The product behaves as single component on thin-layer chromatography (Cellulose F, Merck, 1-butanol-acetic acid-pyridine-water15:3:10:15, v/v).

EXAMPLE 2

Aib—Tyr—Ser—Met—Glu—His—Phe—Arg—Trp—Gly—Lys—Pro—Val—

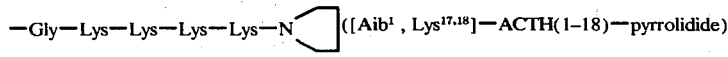([Aib¹, Lys¹⁷,¹⁸]—ACTH(1–18)—pyrrolidide)

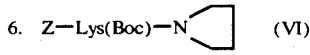  (VI)

To a solution of $N^\alpha$-benzyloxycarbonyl-$N^\epsilon$-t-butyloxy-carbonyl-L-lysine N-hydroxysuccinimide ester (Z-Lys(Boc)-OSu) (1.44 g) in dimethylformamide (5 ml) is added pyrrolidine (0.25 ml) and the mixture is kept at room temperature for 5 hours. The solvent is removed by evaporation in vacuo to give a residue. The residue is dissolved in ethyl acetate and the solution is washed with N/2 hydrochloric acid and M/2 sodium bicarbonate, and after drying over magnesium sulfate, evaporated in vacuo. The resulting product is purified on a column of silica gel (Kiselgel H, Merck, 70 g) using benzene-ethyl acetate-acetic acid (10:30:3 v/v) as solvent. Tubes containing the desired material are pooled and evaporated in vacuo. The residue is precipitated from ether-petroleum ether to give a gelatinous solid. Yield 1.40 g, $[\alpha]_D^{24.5}$ −3.2°±0.9° (c 0.5, methanol).

Anal. Calcd. for $C_{23}H_{35}N_3O_5$: C, 63.72; H, 8.14; N, 9.69. Found: C, 63.94; H, 8.22; N, 9.42.

7. 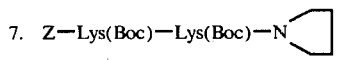  (VII)

Compound VI (1.40 g) is hydrogenolyzed over palladium in methanol containing some acetic acid for 5 hours to give H-Lys(Boc)-pyrrolidide as an oil. This is dissolved in ethyl acetate and Z-Lys(Boc)-OSu (1.44 g) is added at 0° C. The mixture is stirred at 4° C overnight and then is washed with N/2 hydrochloric acid and M/2 sodium bicarbonate, dried over magnesium sulfate and evaporated in vacuo. The resultant product is purified on a column of silica gel (Kiselgel H, Merck, 70 g) using benzene-ethyl acetate-acetic acid (70:30:3 v/v). Tubes containing the desired material are pooled and evaporated in vacuo to give an oil (ca. 2.5 g), which is directly submitted to the subsequent reaction.

8. 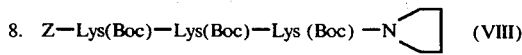  (VIII)

Compound VII (2.5 g) is hydrogenolyzed over palladium in methanol for 4 hours to give H-Lys(Boc)-Lys(-Boc)-pyrrolidide as an oil. This is dissolved in ethyl acetate (20 ml) and Z-Lys(Boc)-OSu (1.44 g) is added at 0° C. The mixture is stirred at 4° C overnight and then is washed with N/2 hydrochloric acid and M/2 sodium bicarbonate, dried over magnesium sulfate and evaporated in vacuo. The residue is crystallized from ether-petroleum ether. Yield 2.60 g, mp. 67°–69° C, $[\alpha]_D^{24.5}$ −21.6°±0.6° (c 1.0, methanol).

Anal. Calcd. for $C_{45}H_{75}N_7O_{11}$: C, 60,72; H, 8.49; N, 11.02. Found: C, 60.62; H, 8.41; N, 11.10.

9. 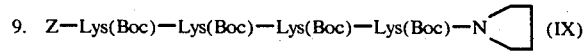  (IX)

Compound VIII (1.10 g) is hydrogenolyzed over palladium in methanol containing some acetic acid for 4 hours to give H-Lys(Boc-Lys(Boc)-Lys(Boc)-pyrrolidide as an oil. This is dissolved in ethyl acetate (10 ml), and Z-Lys(Boc)-OSu (0.583 g) is added at 0° C. The mixture is stirred at 4° C overnight and then is washed with N/2 hydrochloric acid and M/2 sodium bicarbonate, dried over magnesium sulfate and evaporated in vacuo. The residue is precipitated from ether-petroleum ether to give the desired product, yield 1.30 g, mp. 115°–117° C, $[\alpha]_D^{24.5}$ −22.8°±0.6° (c 1.0, methanol).

Anal. Calcd. for $C_{56}H_{95}N_9O_{14}$: C, 60.14; H, 8.56; N, 11.27. Found: C, 60.31; H, 8.68; N, 11.27.

10. Z—Lys(Boc)—Pro—Val—Gly—Lys(Boc)—

—Lys(Boc)—Lys(Boc)—Lys(Boc)—N 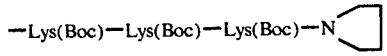      (X)

Compound IX (1.25 g) is hydrogenolyzed over palladium in methanol (50 ml) for 5 hours. The solvent is removed by evaporation in vacuo to give H-Lys(Boc)-Lys(Boc)-Lys(Boc)-Lys(Boc)-pyrrolidide as an oil. This is dissolved in dimethyl-formamide (10 ml) together with Z-Lys(Boc)-Pro-Val-Gly-OH (0.67 g) and N-hydroxysuccinimice (0.105 g). To this solution is then added N,N'-dicyclohexylcarbodiimide (0.187 g) at 0° C and the mixture is stirred at 0° C overnight. The dicyclohexylurea which has separated is removed by filtration and the filtrate is evaporated in vacuo at 40°–45° C. The residue is dissolved in ethyl acetate and the solution is washed with N/2 hydrochloric acid and M/2 sodium bicarbonate, dried over magnesium sulfate and evaporated in vacuo. The resulting residue is precipitated from ether-petroleum ether to give the desired product. Yield 1.40 g, mp. 120°–125° C, $[\alpha]_D^{24.5}$ —46.1°±0.9° (c 1.0, methanol).

Anal. Calcd. for $C_{79}H_{134}N_{14}O_{20} \cdot H_2O$: C, 58.64; H, 8.47; N, 12.12. Found: C, 58.72; H, 8.36; N, 12.26.

of Sephadex G-25 (medium) using a mixed solvent of 1-butanol-acetic acid-pyridine-water (12:3:4:6) as solvent. Five-ml fractions are collected and their peptide contents are monitored with the Folin-Ciocalteu method. Tubes 18–24 and 25–40 are pooled separately, evaporated in vacuo at a bath temperature of 45°–50° C, and lyophilized to give F-1 (115 mg) and F-2 (122 mg), respectively. F-2 is rechromatographed on a column (2.8 × 83 cm) of Sephadex G-25 using the same solvent as above. Tubes 71–95 (4 ml/tube) are pooled, evaporated in vacuo and the residue is lyophilized to give the partially purified octadecapeptide (80 mg).

The peptide is then submitted for further purification to chromatography on a column (2.1 × 21 cm) of carboxymethyl cellulose (Whatman CM-52) using an ammonium acetate buffer (pH 6.5, 2000 ml) with a linear concentration gradient of0–0.6M. Ten-ml fractions are collected and those corresponding to a main peak (tubes 143–157) are pooled, evaporated in vacuo at a bath temperature of 50°–55° C, lyophilized and dried in vacuo over sodium hydroxide pellets and phosphorous pentoxide at 60° C to give a pure preparation of the desired octadecapeptide pyrrolidide. Yield 58 mg, $[\alpha]_D^{24.5}$ —63.5°±2.0° (c 0.5, N/10 acetic acid), thin-layer chromatography (cellulose):homogeneous (to ninhydrin and Ehrlich reagents) in 1-butanol-acetic acid-pyridine-water (15:3:10:15 v/v).

11. Aib—Tyr—Ser—Met—Glu—His—Phe—Arg—Trp—Gly—Lys—

—Pro—Val—Gly—Lys—Lys—Lys—Lys—pyrrolidide   (XI)   [Aib¹ Lys¹⁷,¹⁸]—

—ACTH(1–18)—N 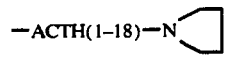

Compound X (0.16 g) is hydrogenolyzed over palladium in methanol (0.16 g) for 5 hours. The solvent is removed by evaporation in vacuo to give $N^\alpha$-free octapeptide pyrrolidide. Boc-Aib-Tyr-Ser-Met-Glu(OBuᵗ)-His-Phe-Arg-Trp-Gly-OH (0.145 g) is dissolved in dimethylformamide (2 ml) and to this is added N hydrochloric acid (0.2 ml). The decapeptide hydrochloride thus formed is precipitated with ether and dried over phosphorus pentoxide in vacuo.

The decapeptide and the octapeptide derivative obtained above are dissolved in dimethylformamide (3 ml), and N-hydroxy-succinimide (0.023 g) is added. To this solution is added N,N'-dicyclohexylcarbodiimide (0.041 g) at 0° C and the mixture is kept at 4° C overnight, and then is introduced into ethyl acetate-ether (1:1 100 ml). The resulting precipitates are filtered off, washed with ethyl acetate and ether and dried in vacuo to afford the crude protected octadecapeptide derivative.

The protected peptide obtained above is dissolved in trifluoroacetic acid (3 ml) together with anisole (0.1 ml) and 2-mercaptoethanol(0.1 ml), and the solution is kept at room temperature for 60 minutes. The precipitates formed upon addition of ether are filtered off, and washed thoroughly with ether and dried. This is dissolved in water (10 ml) and the solution is passed through a column (1.2 × 15 cm) of Amberlite CG-400 (acetate form). The column is washed with portions of water. The elvates are combined and lyophilized to give a crude preparation of the deblocked octadecapeptide.

The crude peptide obtained above is submitted to partition chromatography on a column (2.1 × 75 cm)

Amino acid ratios in acid hydrolysate: Lys 5.45 (5), His 1.07 (1), Arg 1.15 (1), $NH_3$ 0.68 (0), Ser 0.73 (1), Glu 1.00 (1), Pro 1.29 (1), Gly 2.05 (2), Val 1.0 (1), Met 0.99 (1), Tyr 1.04 (1), Phe 1.05 (1). The figures in parenthesis are theoretical values.

EXAMPLE 3

Aib-Tyr-Ser-Met-Glu-His-Phe-Arg-Trp-Gly-Lys-Pro-Val-Gly-Lys-Lys-Lys-Lys-Pro-$NH_2$ ([Aib¹,Lys¹⁷,¹⁸]-ACTH(1–19)-$NH_2$)

12. Z-Lys(Boc)-Lys(Boc)-OMe (XII)

To an ice-cold solution of $N^\alpha$-t-butyloxycarbonyl-L-lysine methyl ester hydrochloride (H-Lys(Boc)-OMe.HCl) (0.89 g, 3 mmoles) and triethylamine (0.46 ml, 3.3 mmoles) in dimethyl-formamide (8 ml) is added $N^\alpha$-benzyloxycarbonyl-$N^\epsilon$-t-butyloxy-carbonyl-L-lysine N-hydroxysuccinimide ester (Z-Lys(Boc)-OSu) (1.43 g, 3 mmoles) (Bull. Chem. Soc. Japan 39, 882 (1966)) and the mixture is allowed to stand at 4° C overnight followed by evaporation in vacuo at a bath temperature of 40° C. The residue is dissolved in ethyl acetate and the solution is washed successively with ice-cold M hydrochloric acid, water, and M sodium bicarbonate, dried over magensium sulfate and evaporated in vacuo to give a residue, which is precipitated from ethyl acetate-petroleum ether. Reprecipitation from the same solvent yields the desired product in pure form; yield 1.80 g (96.5%), $[\alpha]_D^{22.5}$—11.7°±0.5° (c 1.0, methanol). Thin-layer chromatography (silica gel): homogeneous (to ninhydrin after pretreatment with hydrobromic acid) in chloroform-methanol-acetic acid (90:10:3, v/v).

Anal. Calcd. for $C_{31}H_{50}N_4O_9$: C, 59.79; H, 8.09; N, 9.00. Found: C, 59.55; H, 7.96; N, 8.97.

13. Z-Lys(Boc)-Lys(Boc)-NHNH$_2$ (XIII)

Compound XII (1.50 g, 2.4 mmoles) is dissolved in ethanol (10 ml) and hydrazine hydrate (1.16 ml, 24 mmoles) is added. The mixture is allowed to stand at room temperature for 24 hours and then evaporated in vacuo. The resulting solid residue is dissolved in water-saturated ethyl acetate and the solution is washed with water two times and quickly dried over magnesium sulfate. The crystalline precipitates which separated upon standing at room temperature are filtered off, washed with ether and dried in vacuo. Recrystallization from ethyl acetate-ether affords the hydrazide XIII in pure form; yield 1.41 g (94%), mp. 121°–123° C, $[\alpha]_D^{22.5}$ −8.5°±0.5° (c 1.0, dimethylformamide), −18.2°±0.6° (c 1.0, methanol).

Anal. Calcd. for $C_{30}H_{59}N_6O_8$: C, 57.86; H, 8.09; N, 13.50. Found: C, 57.61; H, 8.05; N, 13.36.

14. H-Pro-NH$_2$ (XIV)

Benzyloxycarbonyl-L-proline amide (Z-Pro-NH$_2$)(1.24 g) is dissolved in acetic acid (5 ml) and M hydrogen chloride in acetic acid (6 ml) is added. The solution is submitted to catalytic hydrogenolysis over palladium for 3.5 hours. Removal of the solvent yields a sirupy residue, which is crystallized from ether. The collected precipitates are recrystallized from methanol-ether; yield 0.68 g (91%), $[\alpha]_D^{22}$ −68.2°±1.1° (c 1.0, methanol).

Anal. Calcd. for $C_5H_{10}N_2O \cdot HCl$: C, 39.87; H, 7.36; N, 18.60; Cl, 23.54. Found: C, 39.93; H, 7.44; N, 18.67; Cl, 23.54.

15. Z-Lys(Boc)-Lys(Boc)-Pro-NH$_2$ (XV)

A solution of compound XIII (1.25 g, 2 mmoles) in dimethylformaide (8 ml) is chilled to −40° C to −50° C in a Dry-ice-acetone bath and 3.66M hydrogen chloride in dioxane (1.37 ml) is added. To this is then added dropwise isoamyl nitrite (0.29 ml, 2.2 mmoles) and the mixture is stirred at −10° C to −20° for 10 minutes. The mixture is again chilled to −40° C to −50° C and an ice-cold solution of XIV (0.30 g, 2 mmoles) and triethylamine (1.1 ml, 7.7 mmoles) in dimethylformamide (10 ml) is introduced. The temperature is allowed to rise to 0° C, at which the mixture is stirred for 3 hours. After the pH have been adjusted to about 8 with an additional quantity of triethylamine (0.27 ml, 2 mmoles) the reaction mixture is kept at 4° C for 2 days. The solvent is removed by evaporation in vacuo at a bath temperature of 40° C. The resulting residue is dissolved in ethyl acetate and the solution is washed with ice-cold M hydrochloric acid and M sodium bicarbonate, dried over magnesium sulfate and evaporated in vacuo. Repeated precipitation of the residue obtained above yields the desired tripeptide XV; yield 1.29 g (91%), mp. 85°–90° C, $[\alpha]_D^{22}$ −40.5°±0.4° (c 2.0, methanol).

Anal. Calcd. for $C_{35}H_{56}N_6O_9$: C, 59.64; H, 8.01; N, 11.92. Found: C, 59.75; H, 8.08; N, 11.66.

16. Z-Lys(Boc)-Lys(Boc)-Lys(Boc)-Pro-NH$_2$ (XVI)

Compound XV (1.06 g, 1.5 mmoles) is hydrogenolyzed over palladium in methanol for 3 hours. After the solvent have been removed by evaporation in vacuo the residue is dissolved in ethyl acetate and chilled in an ice bath. To this is added $N^\alpha$-benzyloxycarbonyl-$N^\epsilon$-t-butyloxycarbonyl-L-lysine N-hydroxy-succinimide (0.72 g, 1.5 mmoles) and the mixture is stirred at 4° C overnight. The precipitates which has separated are filtered off, washed with ice-cold ethyl acetate and dried in vacuo (1.31 g). An additional quantity of the product is obtained upon concentration of the filtrate (0.08 g). The combined precipitates are dissolved in methanol and most of the solvent is removed by evaporation in vacuo. The resulting sirupy residue is precipitated from ethyl acetate (20 ml)-ether (20 ml); yield 1.35 g (96%).

17. Z-Lys(Boc)-Pro-Val-Gly-Lys(Boc)-Lys(Boc)-Lys(Boc)-Lys(Boc)-Pro-NH$_2$ (XVII)

Compound XVI (0.37 g, 0.4 mmole) is hydrogenolyzed over palladium in methanol for 3.5 hours. Removal of the solvent by evaporation in vacuo yields a foamy residue, which is dried over soduum hydroxide pellets and phosphorous pentoxide.

A solution of $N^\alpha$-benzyloxycarbonyl-$N^\epsilon$-t-butyloxycarbonyl-L-lysyl-L-prolyl-L-valyl-glycyl-$N^\alpha$-t-butyloxycarbonyl-L-lysine hydrazine (Z-Lys (Boc)-Pro-Val-Gly-Lys(Boc)-NHNH$_2$)(0.35 g, 0.4 mmole) in dimethylformamide (3 ml) is chilled in a Dry Ice acetone bath (−40° C to −50° C) and 3.66M hydrogen chloride in dioxane (0.27 ml, 1 mmole) is added. To this is added isoamyl nitrite (0.057 ml, 0.44 mmole dropwise and the mixture is then stirred at −10° C to −20° C for 10 minutes. The mixture is again chilled to −40° C to −50° C and an ice-cold solution of $N^\alpha$-t-butyloxycarbonyl-L-lysyl-$N^\epsilon$-t-butyloxycarbonyl-L-lysyl-$N^\epsilon$-t-butyloxycarbonyl-L-lysysl-L-proline amide (H-Lys(Boc)-Lys(Boc)-Lys(Boc)-Pro-NH$_2$) obtained above and triethylamine (0.16 ml, 1.5 mmoles) in dimethylformamide (2 ml) is introduced. The temperature is allowed to rise to 4° C, at which the reaction mixture is stirred for 2.5 days. The solvent is removed by evaporation in vacuo at a bath temperature of 45° C. The residue is dissolved in water-saturated ethyl acetate and M sodium bicarbonate, dried over magnesium sulfate and evaporated in vacuo. The resulting residue is dissolved in hot ethyl acetate and the desired product is precipitated by the addition of ether and petroleum ether. Reprecipitation from hot ethyl acetate-isopropyl ether gives a pure preparation of the nonapeptide XVII, yield 0.59 g (90%), $[\alpha]_D^{23}$ −57.3°±2.3° (c 0.4, methanol). Thin-layer chromatography (silica gel): homogeneous to ninhydrin after pretreatment with hydrochloric acid in chloroform-methanol (8:2 v/v).

Anal. Calcd. for $C_{80}H_{135}N_{15}O_{21}$: C, 58.48; H, 8.28; N 12.79. Found: C, 58.30; H, 8.62; N, 12.74.

18. H-Aib-Tyr-Ser-Met-Glu-His-Phe-Arg-Trp-Gly-Lys-Pro-Val-Gly-Lys-Lys-Lys-Lys-Pro-NH$_2$([Aib$^1$,17, 1817,18]-ACTH(1-19)-NH$_2$ (XVIII)

Compound XVII (120 mg, 0.073 mmole) is dissolved in methanol and the solution is submitted to catalytic hydrogenolysis over palladium for 3.5 hours. Removal of the solvent by evaporation in vacuo affords a foamy residue, which is dried in vacuo to give the $N^\alpha$-free nonapeptide derivative. To this is added a solution of Z-Aib-Tyr-Ser-Met-Glu(OBzl)-His-Phe-Arg(NO$_2$)-Trp-Gly-OH(120 mg, 0.073 mmole, $[\alpha]_D^{22.5}$ −20.5° ±0.7° (c 1.0, 50% acetic acid) (prepared from Z-Aib-Tyr-Ser- Met-NHNH₂ and H-Glu(OBzl)-His-Phe-Arg(NO₂(Trp-Gly-OH by the azide method), and N-hydroxysuccinimide (16.8 ml, 0.146 mmole) in dimethylformamide (2 ml) and is then added, N,N'-dicyclohexylcarbodiimide (60.3 mg, 0.292 mmole) with dimethylformamide (2 ml) as solvent. The resulting mixture is kept at 4° C for 2.5 days. N,N'-Dicyclohexylurea which have separated is filtered off and the filtrate is introduced into ethyl acetate (50 ml). After addition of an equal volume of ether the precipitates are filtered off, washed with ethyl acetate and ether and dried in vacuo (218 mg).

The crude product obtained above is treated with hydrogen fluoride (ca. 15 ml) at 0° C for 60 min in the presence of methionine (100 mg) and anisole (0.23 ml) followed by evaporation in vacuo at 0° C. The residue is dissolved in ice-cold water (10 ml) and the solution is, after washing with ethyl acetate, passed through a column (1.2 × 18 cm) of Amberlite CG-400 (acetate form) with portions of water. The effluents are combined, concentrated in vacuo at a bath temperature of 50° C and lyophilized (345 mg). This is then submitted to chromatography on a column (1.7 × 30 cm) of carboxymethyl cellulose (Serva, 0.63 meq/g) with an ammonium acetate buffer (pH 6) having a linear concentration gradient of 0 – 0.6M (2000 ml). The fractions (10 ml/tube) are monitored at 280 nm. Those corresponding to a major peak (tubes 98–135) are combined, evaporated in vacuo at a bath temperature of 50° C and lyophilized to yield the partially purified nonadecapeptide (111 mg).

For further purification the preparation obtained above is chromatographed on a column (1.7 × 37 cm) of Sephadex G-25 (medium) using a solvent system of 1-butanol-acetic acid-pyridine-water (12:3:4:6, v/v). The fractions (3.6 ml/tube) are examined by thin-layer chromatography on cellulose plates (Merck) with 1-butanol-acetic acid-pyridine-water (15:3:10:15, v/v) as solvent; dimethylamino-benzaldehyde (Ehrlich reagent) having been used for detection. Tubes 23–40 are combined, evaporated in vacuo at a bath temperature of 50° C and lyophilized (71 mg). This is again submitted to a carboxymethyl cellulose column (Whatman CM-52, 1.7 × 18 cm) using an ammonium acetate buffer (pH 6) with a linear concentration gradient of 0–0.6M (1500 ml). The fractions (tubes 141–170, 7.2 ml/tube) corresponding to a single peak are combined, evaporated in vacuo and lyophilized to constant weight; yield 68 mg, $[\alpha]_D^{24.5}$ −75.9°±2.4° (c 0.5, M/10 acetic acid), thin-layer chromatography (cellulose): homogeneous (to ninhydrin and Ehrlich reagents) in 1-butanol-acetic acid-pyridine-water (15:3:10:15, v/v).

$\lambda_{max}^{0.1M\text{-}HCl}$ 280 nm ($\Sigma_{1cm}^{1\%}$ 23.0), $\lambda_{shoulder}^{0.1M\text{-}HCl}$ 289 nm ($\Sigma_{1cm}^{1\%}$ 17.0);

$\lambda_{max}^{0.1M\text{-}NaOH}$ 282 nm ($\Sigma_{1cm}^{1\%}$ 25.0), $\lambda_{max}^{0.1M\text{-}NaOH}$ 289 nm ($\Sigma_{1cm}^{1\%}$ 24.0).

Amino acid ratios in acid hydrolysate: Lys 5.08 (5), His 0.98 (1), Arg 1.03 (1), Ser 0.92 (1), Glu 1.01 (1), Pro 2.07 (2), Gly 1.96 (2), Aib 0.93 (1), Val 1.00 (1), Met 1.02 (1), Tyr 0.97 (1), Phe 1.01 (1). Trp/Tyr ratio was determined spectrophotometrically to be 1.0. The figures in parentheses are theroretical values.

What we claim is:

1. A member selected from the group consisting of

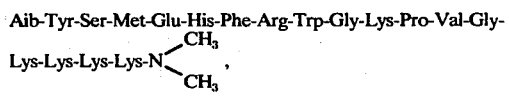

a non-toxic acid addition salt thereof, and a complex thereof.

2. A compound according to claim 1 said compound being

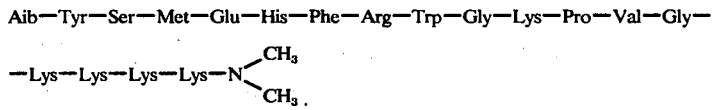

3. A member selected from the group consisting of

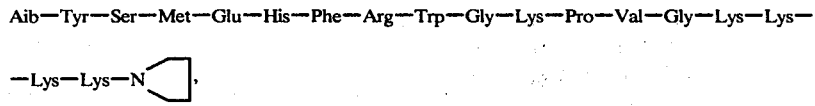

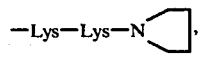

a non-toxic acid addition salt thereof, and a complex thereof.

4. A compound according to claim 3, said compound being

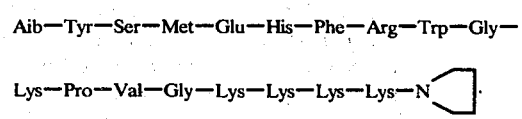

* * * * *